United States Patent [19]

Sugano et al.

[11] 4,352,726
[45] Oct. 5, 1982

[54] ION SELECTIVE FIELD-EFFECT SENSOR

[75] Inventors: Takuo Sugano; Eiji Niki; Yoichi Okabe; Tatsuo Akiyama, all of Tokyo, Japan

[73] Assignee: Takashi Mukaibo, Tokyo, Japan

[21] Appl. No.: 201,637

[22] Filed: Oct. 28, 1980

Related U.S. Application Data

[63] Continuation of Ser. No. 20,686, Mar. 15, 1979, abandoned.

[30] Foreign Application Priority Data

Sep. 14, 1978 [JP] Japan .................. 53-112339

[51] Int. Cl.$^3$ .......................................... G01N 27/30
[52] U.S. Cl. .......................... 204/195 M; 204/1 T; 357/25
[58] Field of Search ............. 204/195 M, 1 T; 357/25; 128/2 E, 635

[56] References Cited

U.S. PATENT DOCUMENTS

| | | | |
|---|---|---|---|
| 3,706,649 | 12/1972 | Cosgrove et al. | 204/195 M |
| 3,715,297 | 2/1973 | Cosgrove et al. | 204/195 M |
| 3,824,215 | 7/1974 | Takeoshi et al. | 260/52 |
| 4,020,830 | 5/1977 | Johnson et al. | 128/635 |

FOREIGN PATENT DOCUMENTS 52-109593 9/1977 Japan .
52-109600 9/1977 Japan .

OTHER PUBLICATIONS

C. J. Pedersen, J. Am. Chem. Soc., vol. 89, pp. 7017-7036, (1967).
Jiri Janata et al., Biomed. Engineering, pp. 241-245, Jul. 1976.
Stanley D. Moss et al., Anal. Chem., vol. 47, No. 13, pp. 2238-2243, (1975).
E. Blasius et al., J. Chromatography, 96, 89-97, (1974).
T. Akiyama et al., Third Japan-USSR Seminar on Electrochemistry, Oct. 28-Nov. 1, 1978.
J. Polymer Science, vol. 9, part A-1, No. 1, p. 817, Jan. 1971.
Macromolecules, vol. 4, No. 3, pp. 359-360, (1971).
Tadayoki Matsuo et al., Ohyo Butsuri, vol. 49, No. 6, pp. 586-593, (1980).

*Primary Examiner*—G. L. Kaplan
*Attorney, Agent, or Firm*—Sughrue, Mion, Zinn, Macpeak and Seas

[57] ABSTRACT

An ion selective field-effect sensor selectively sensitive to a particular cation to be measured is disclosed. In the sensor is used a giant heterocyclic compound selectively forming a complex with the particular cation as an ion sensitive film provided on a surface of a field-effect semiconductor device.

16 Claims, 11 Drawing Figures

FIG_1

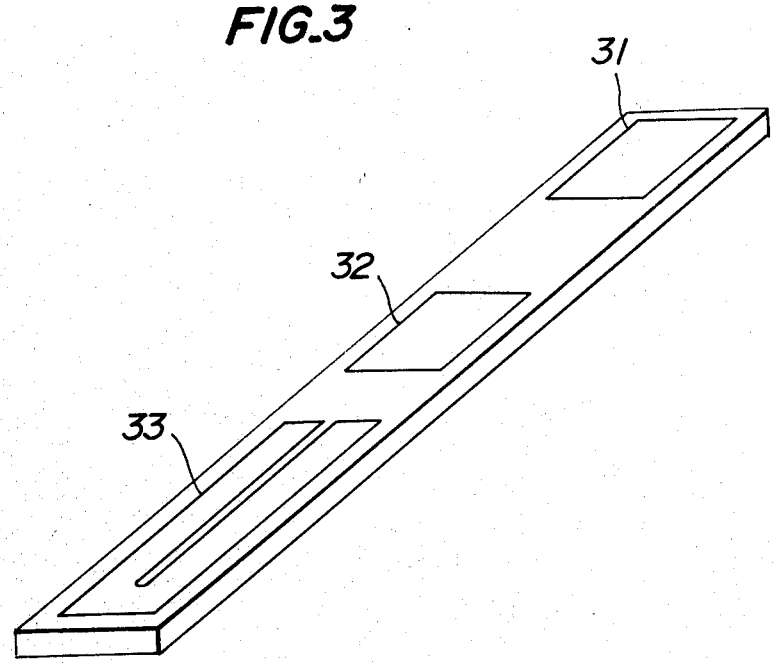

ION SELECTIVE FIELD-EFFECT SENSOR

This is a continuation, of application Ser. No. 20,686, filed Mar. 15, 1979 and now abandoned.

This invention relates to an electrode element having a selective sensitivity to a particular cation. More particularly, it relates to a cation-selective field-effect sensor comprising a semiconductor provided at its surface with a giant heterocyclic compound capable of selectively forming a complex with a particular cation.

Heretofore, qualitative or quantitative measurement of a cation in a solution has been performed by a chemical analysis using various reagents, a colorimetric analysis, a spectrophotometric analysis, an electroanalysis measuring an electrical conductance, an atomic-absorption method or the like, but these processes are not suitable for measuring an ion concentration in a very short time or continuously. Moreover, in the electroanalysis, it makes possible to measure the electrical conductance in a very short time, but the separate measurement of ionic species is impossible.

In addition to the above processes, there has recently been proposed a process wherein an electrode assembly composed of a reference electrode and an electrode element having a selective sensitiveness to a particular cation as an indicating electrode is immersed into a sample solution to measure a potential difference between the electrodes, which is practically used for the measurement of certain ions. As such an ion selective electrode, there are a solid membrane type ion electrode, a liquid membrane type ion electrode and so on. The use of solid membrane type ion electrode has such a drawback that it is necessary to make the electrode large in order to reduce an internal resistance and improve a reproducibility and hence a relatively large amount of a sample solution is required. On the other hand, the use of the liquid membrane type ion electrode has such a drawback that a solute must be periodically supplemented because it is apt to be influenced by a pressure of a solution to be measured and the like.

Lately, it has been found that a certain natural antibiotic having a giant cyclic structure, which is called as a macrolide, incorporates selectively a particular cation in voids of its cyclic structure to form a stable complex. Among such natural macrolides, valinomycin having a large cation-incorporating ability against K+ is attempted to be used as a neutral carrier in an ion selective electrode element. However, when valinomycin is used in the liquid membrane type ion electrode as a neutral carrier, there is a drawback that a solute must be periodically supplemented like the conventional liquid membrane type electrode. Further, when valinomycin is dispersed in polyvinyl chloride resin containing a plasticizer to form a plastic-supported membrane electrode, it dissolves out in a sample solution, whereby a potential is undesirably changed.

Up to now, various giant heterocyclic compounds are synthesized as a synthetic substance having a structure similar to the natural macrolide and selectively forming a complex with a cation and there are positively made studies with respect to the properties of these compounds. A typical example of such compounds includes a group of large cyclic polyethers called as a crown ether. Since the giant heterocyclic compound is a synthetic substance, it makes possible to design its chemical structure so as to have a selectivity to a particular cation and synthesize various derivatives thereof.

The inventors have considered that if the giant heterocyclic compound is fixed to an electrode element produced by an advanced MOS-IC technique, there is obtained an ion selective electrode element solving the aforementioned drawbacks of the prior art and a practically simple construction and a wide application range and have made concrete studies with respect to a process for fixing the compound to the electrode element and as a result, the invention has been accomplished.

It is an object of the invention to provide an ion selective field-effect sensor comprising an ion selective electrode element wherein concentration and activity of a particular cation can quantitatively be analyzed in a short time only by contacting the ion selective electrode element with a solution to be measured, which contains several cations, without modifying the nature of the solution.

The ion selective electrode element according to the invention is characterized by being a solid element containing no solution and having a supermicro and durable structure and a fast response speed.

The invention will now be described in greater detail with reference to the accompanying drawings, wherein:

FIG. 3 is a schematically perspective view illustrating a concept of a finished sensor according to the invention as a whole;

FIG. 4b is an enlarged view showing a part of the sensor according to the invention of FIG. 4a.

Figure 1:
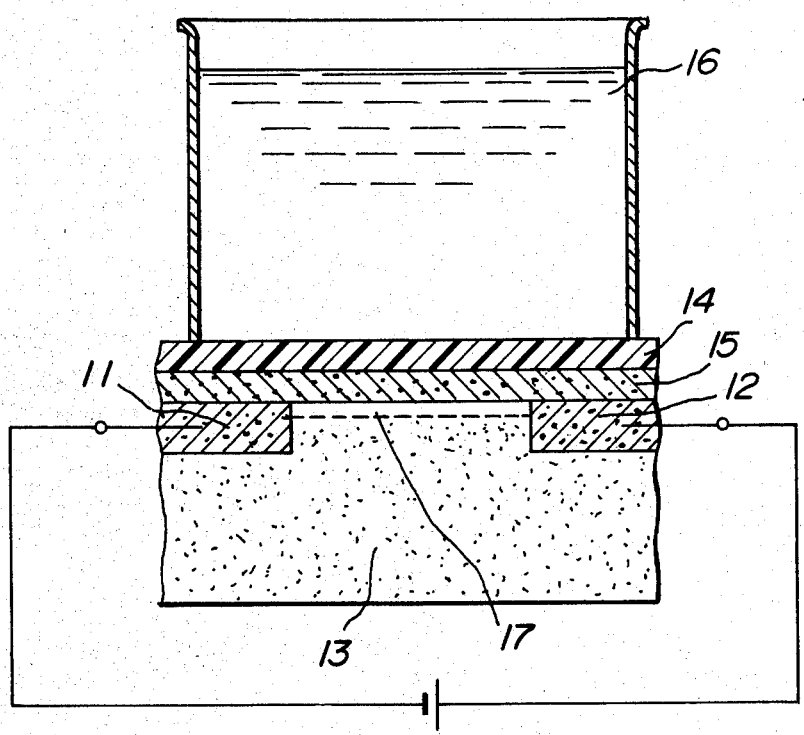
FIG. 1 is a schematic sectional view illustrating a theory of an ion selective electrode element constituting the ion selective field-effect sensor according to the invention.

In FIG. 1 is diagrammatically illustrated a theory of an ion selective electrode element constituting the ion-sensitive field-effect sensor according to the invention.

The operating theory of the field-effect sensor (ion selective electrode element) is easy to be understood when comparing with an operating theory of an MOS field-effect transistor.

Referring to FIG. 1, numeral 11 is a source and numeral 12 is a drain. The source 11 and drain 12 are rendered to N-type by addition of a donor when a semiconductor substrate 13 is P-type or to P-type by addition of an acceptor when the substrate 13 is N-type. Numeral 14 is an ion selective insulating film, which is a thin film of an insolubilized giant heterocyclic compound or is obtained by shaping powder of the insolubilized giant heterocyclic compound with a binder into a thin film. If desired, another insulating film 15 such as silicon oxide film, silicon nitride film or the like may be inserted between the semiconductor substrate 13 and the insulating film 14. In the MOS field-effect transistor, metal electrodes are provided on these insulating films and a given voltage is applied thereto, whereby a density of carriers in a channel is controlled. On the contrary, in the ion selective electrode element according to the invention, a solute solution 16 to be measured is made into contact with the ion selective insulating film 14 instead of the metal electrode and consequently the carrier density in a channel 17 is changed by space charge penetrated from the solution 16 into the film 14, which is measured as a change of drain current.

Figure 2:
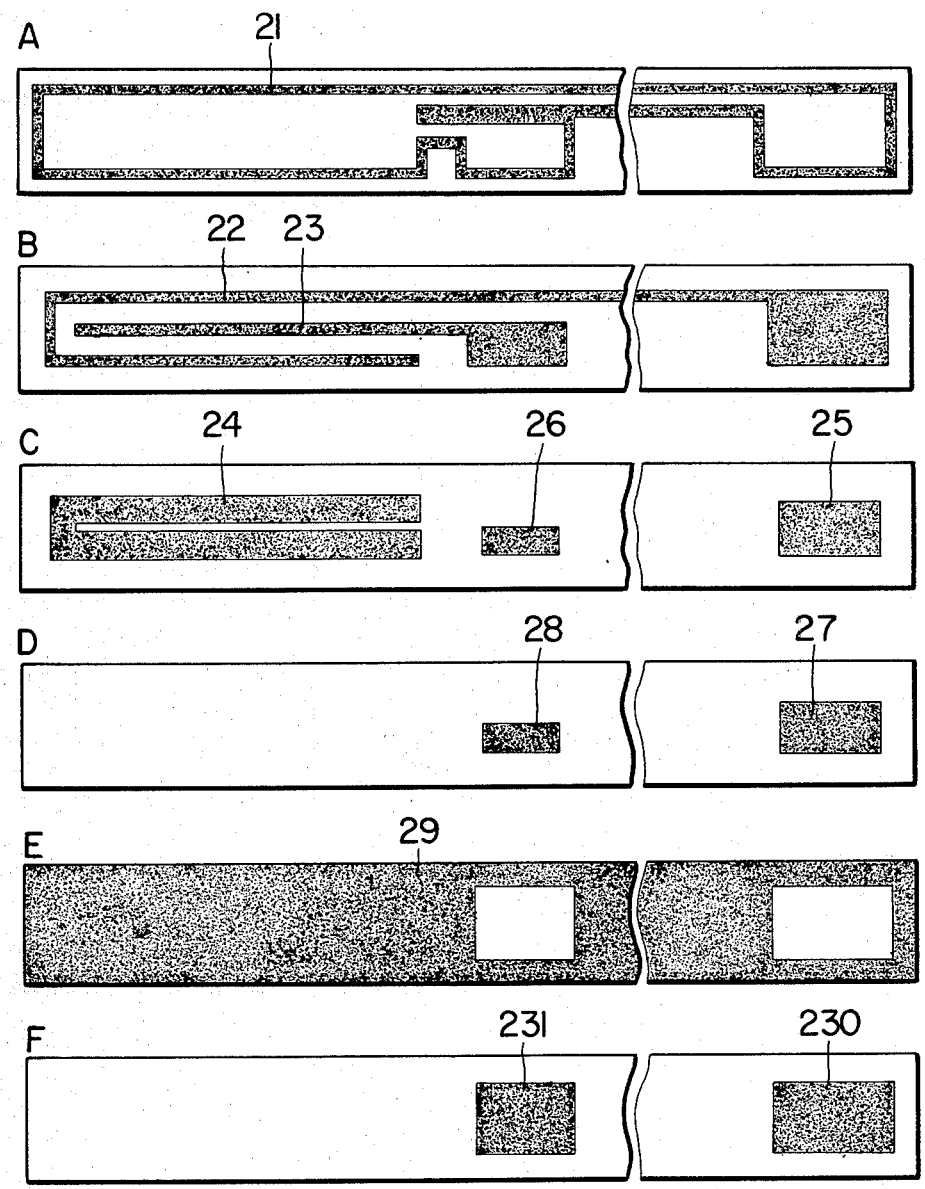
FIG. 2 is a schematic plan view of a mask having various patterns used in the production of the ion selective electrode element.

In FIG. 2 are shown various masks having patterns used in the production of an embodiment of the ion selective electrode element according to the invention as mentioned below:

Mask A has a pattern 21 for the formation of a channel stopper;

Mask B has patterns 22, 23 for the formation of a source and a drain;

Mask C has a pattern 24 for the exposure of the channel and patterns 25, 26 for the formation of holes of the source and drain electrodes;

Mask D has patterns 27, 28 for the formation of holes of the source and drain electrodes after an insulating film is formed on the surface of the channel;

Mask E has a pattern 29 for the removal of unnecessary part of aluminium; and

Mask F has patterns 230, 231 for the formation of holes of the source and drain electrodes after the formation of an insulating film.

The production of the ion selective electrode element is carried out by using these masks A-F as follows:

(1) Pre-treatment

| Wafer to be used: | P-type (100) substrate, Diameter 40 mm, Thickness 200μ, Specific resistance 3–5 Ωcm |
|---|---|

(a) ultrasonic cleaning with pure water (2 minutes)
   Dusts are removed from the surface of the wafer.
(b) ultrasonic cleaning with acetone (2 minutes)
   Organic substances are removed.
(c) boiling with trichlene (10 minutes, two times)
   The surface of the wafer is degreased to be rendered to hydrophobic nature and inactivation.
(d) ultrasonic cleaning with acetone (2 minutes)
   Trichlene is removed.
(e) ultrasonic cleaning with ethanol (2 minutes)
   Acetone is removed.
(f) drying (using a spinner)
(g) boiling with a 1:1 solution of $HNO_3$ and $H_2SO_4$ (10 minutes)
   Heavy metals are removed.
(h) ultrasonic cleaning with deionized water (2 minutes)
(i) drying (using a spinner)
(j) etching with a 1:10 solution of HF and $H_2O$ (20 seconds)
   Lower oxides are removed.
(k) ultrasonic cleaning with pure water (2 minutes)
(l) drying (using a spinner)

(2) Thermal oxidation (in wet oxygen)
The wafer is oxidized in an oxidation furnace under a wet oxygen atmosphere (through a bubbler filled with pure water of 100° C. at a flow rate of 1 l/min). When the oxidation is performed at a temperature of 1,150° C. for 40 minutes, the resulting oxide film has a thickness of 6,600 Å.
This film is used as a mask for the selective diffusion of boron.

(3) First photolithography (using mask A)

The pattern of the mask A is transferred onto the wafer by using a photoresist, a photomask and an exposure equipment.
(a) application of photoresist
   The photoresist is directly applied on the wafer and the thickness of the photoresist film is made uniform by means of a spinner. The thickness is 2–3μ at a rotating speed of 3,000 rpm for a spinning time of 30 seconds.
(b) pre-baking
   The organic solvent is evaporated from the photoresist by heating with an infrared ray lamp to harden the resist.
   Temperature 85°–90° C. Time 30 minutes
(c) exposure
   The pattern of the mask A is baked on the resist by means of a table exposure device.
   Exposure time 8.0 seconds.
(d) development and rinsing
   The unexposed portion of the resist is removed with a developing solution for the photoresist and then the developing solution is washed out with a rinsing solution.
(e) post-baking
   The wafer is heated in a baking furnace to strengthen the adhesion between the resist and the wafer.
   Temperature 120°–140° C., Time 30 minutes (4) Etching
(a) The oxide film is etched with an HF buffer solution ($HF:NH_4F:H_2O = 10$ cc:20 g:30 cc).
   Temperature 20° C., Time 5 minutes
(b) removal of photoresist
   The photoresist is removed with a stripper for the photoresist.
   Temperature 120° C., Time 3–4 minutes
(c) cleaning
   The ultrasonic cleaning is performed with trichlene (trichloroethylene), acetone, isopropanol and pure water in this order and the drying is performed by means of a spinner.

(5) Diffusion of boron
The selective diffusion of boron is performed by using the pattern of the oxide film formed at the aforementioned step as a mask to form a channel stopper.
(a) pretreatment of BN wafer
   The BN wafer is oxidized in a dry oxygen atmosphere to produce $B_2O_3$ on the surface thereof according to the following reaction formula:

$$4BN + 3O_2 \rightarrow 2B_2O_3 + 2N_2 \uparrow$$

Temperature 1,000° C., Time 30 minutes, P2 Flow rate of oxygen 1 l/min.
(b) pre-deposition
   The BN wafer and Si wafer are placed together in a diffusion furnace and heated in a dry nitrogen atmosphere, whereby $B_2O_3$ is evaporated from the surface of the BN wafer and deposited on the Si wafer at a surface concentration necessary for redistribution of boron.
   Temperature 500° C., Time 10 minutes,
   Flow rate of nitrogen 1 l/min.
(c) driving-in
   The redistribution of the deposited boron is performed by heating at an elevated temperature.
   Temperature 1,100° C., Time 60 minutes, Flow rate of nitrogen 1 l/min.
In this case, the density of the impurity on the surface of the Si wafer is about $3 \times 10^{17}$ cm$^{-3}$.

(d) removal of oxide film
The oxide film is removed from the surface of the Si wafer with a 1:1 solution of HF and H$_2$O. Time 3–4 minutes.

(6) Thermal oxidation (in wet oxygen)
This step is carried out in the same manner as described in the step (2). The resulting oxide film is used as a mask for the selective diffusion of N+-type source and drain regions.

(7) Second photolithography (using mask B)
This step is carried out in the same manner as described in the step (3). In this case, the mask B should be registered with the mask A in the exposure, so that the pattern of the mask B is superposed on the pattern formed at the step (5).

(8) Etching
This step is carried out in the same manner as described in the step (4).

(9) Diffusion of phosphorus
This step is performed by using a diffusion source called as O.C.D. (Tokyo Oka Coating Diffusion Source).

(a) application of O.C.D.
The diffusion source is directly applied on the wafer and the thickness of the coating is made uniform by means of a spinner. The thickness is about 1 μ at a rotating speed of 5,000 rpm for a spinning time of 30 seconds.

(b) pre-baking (deposition)
The heating is performed with an infrared ray lamp.
Temperature 150° C., Time 20 minutes (c) driving-in
The redistribution of phosphorus is performed by heating at an elevated temperature.
Temperature 1,100° C., Time 40 minutes,
Flow rate of nitrogen 1 l/min
In this case, the density of the impurity on the surface of the wafer is about $4 \times 10^{19}$ cm$^{-3}$.

(d) removal of oxide film
The oxide film is removed with a 1:1 solution of HF and H$_2$O. Time 3–4 minutes

(10) Thermal oxidation (in wet oxygen)
This step is carried out in the same manner as described in the step (2). The resulting oxide film is a field oxide film.

(11) Third photolithography (using mask C)
This step is carried out in the same manner as described in the step (7).

(12) Etching
This step is carried out in the same manner as described in the step (4). The resulting opening is used in the formation of oxide film for gate.

(13) Thermal oxidation (in dry oxygen)
The oxide film for gate is formed by oxidation in a dry oxygen atmosphere.
Temperature 1,150° C., Time 20 minutes
The resulting oxide film has a thickness of 500 Å.

(14) Sputtering
A film of Si$_3$N$_4$ having a thickness of about 300 Å is formed on SiO$_2$ film produced in the step (13) by sputtering Si$_3$N$_4$ in N$_2$ by means of a sputtering equipment.

(15) Chemical vapor deposition
A film of SiO$_2$ is further formed on Si$_3$N$_4$ film by CVD method. The gas to be used is SiH$_4$ and N$_2$ and the temperature is 600° C. The resulting SiO$_2$ film is used as a mask for etching of Si$_3$N$_4$.

(16) Fourth photolithography (using mask D)
This step is carried out in the same manner as described in the step (7).

(17) Etching
This step is carried out in the same manner as described in the step (4). The resulting opening is used for etching of Si$_3$N$_4$.

(18) Etching
Si$_3$N$_4$ is etched out by using H$_3$PO$_4$ heated at 180° C. Time 5–6 minutes.

(19) Etching
The etching of SiO$_2$ is performed with a buffer HF to form a hole for contact and at the same time SiO$_2$ provided on the surface of Si$_3$N$_4$ is etched.

(20) Vacuum deposition of Al
An aluminum film used for the electrode is formed by vacuum deposition.
Pump down the vacuum chamber to at least $5 \times 10^{-6}$ Torr.

(21) Fifth photolithography (using mask E)
This step is carried out in the same manner as described in the step (4).

(22) Etching of Al
Drain and source electrodes are formed by etching of Al.

(a) etching with aluminum etchant
The etchant has a mixing ratio of H$_3$PO$_4$:CH$_3$COOH:HNO$_3$:H$_2$O = 15:5:1:1.
Temperature 40° C., Etching time 3 minutes (b) removal of photoresist
The photoresist is removed by means of the stripper.
Temperature 100° C., Time 1–2 minutes (c) cleaning
The cleaning is performed with trichlene, acetone, isopropanol and deionized water in this order under slight stirring.

(23) Annealing
An ohmic contact at a boundary between Al and Si is formed by heating in an atmosphere of a forming gas (N$_2$ 90%, H$_2$ 10%).
Temperature 400° C., Time 60 minutes

(24) Application of crown ether
The crown ether is applied on the surface of the resulting FET and fixed thereto.

(a) application of crown ether
The crown ether is applied by means of a spinner. Thickness about 1μ.

(b) pre-curing
The pre-curing is performed at 80° C. for 15 hours.

(c) after-curing
The after-curing is performed at 120° C. for 5 hours.

(d) cleaning
The cleaning is performed with hot water of 80° C.

(e) drying
The drying is performed at 120° C. for 15 hours.

(25) Sixth photolithography (using mask F)
This step is carried out in the same manner as described in the step (4).

(26) Etching of crown ether
The drain and source electrodes are worked by etching of crown ether.

(a) ion shower

The unnecessary portion of crown ether is scraped by means of ion shower.

(b) removal of photoresist

The photoresist is removed by means of a stripper. Temperature 100° C., Time 1-2 minutes.

(c) cleaning

The cleaning is performed with trichlene, acetone, isopropanol and pure water in this order under slight stirring.

In FIG. 3 is shown a perspective view of a finished sensor according to the invention, wherein numeral 31 is a source (or drain), numeral 32 is a drain (or source) and numeral 33 is an ion selective measuring region.

Figure 4A:
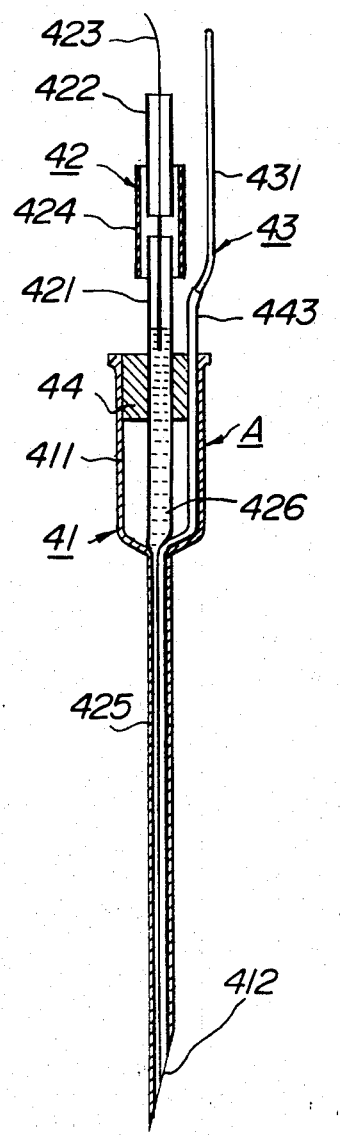
FIG. 4a is a side view partly shown in section of a complete assembly encapsulating the sensor according to the invention.
Figure 4B:
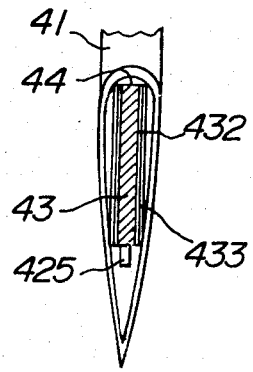

In FIGS. 4a and 4b is shown a state of encapsulating the sensor according to the invention into a practical measuring device, wherein FIG. 4a shows a whole of the device and FIG. 4b shows an enlargement of a part of the sensor.

The ion selective electrode assembly A comprises a reference electrode member 42 and a measuring electrode member (field-effect sensor) 43, which are inserted into a needle 41 of a syringe.

The reference electrode member 42 comprises a supporting tube 421 made of an insulating material such as glass or the like. The upper end of the tube 421 is connected through an insulative tube 424 such as silicone tube or the like to a lower end of a holder 422 supporting an internal reference electrode 423 therein. At lower end of the supporting tube 421 is provided an elongated cylindrical part 425 having a very small diameter. A standard solution 426 is filled in the supporting tube 421 and the elongated cylindrical part 425 until it contacts with a free end of the internal reference electrode 423.

The internal reference electrode 423 is preferably a standard Ag-AgCl electrode. As the standard solution 426 is used a solution of lithium trifluoroacetate, lithium trichloroacetate, sodium chloride, lithium chloride or the like, which does not influence on the concentration of K+ in a sample solution .

The measuring electrode member 43 comprises the field-effect sensor according to the invention as mentioned above and an insulative coating 433 made of polyvinyl chloride resin or the like covering the sensor.

As a substance forming a solid sensitive film 432 is used an insolubilized polymer obtained by the polymerization of a giant heterocyclic compound selectively forming a complex with a cation to be measured. The giant heterocyclic compound is selected from compounds having the following formula:

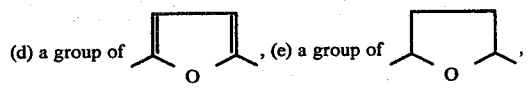

wherein X and Y are the same or different and represent
 (a) a divalent aliphatic hydrocarbon residue,
 (b) a divalent aromatic hydrocarbon residue,
 (c) a divalent alicyclic hydrocarbon residue, (d) a group of 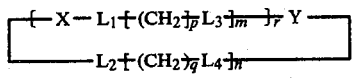, (e) a group of (f) a group of 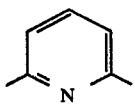 or (g) a divalent group of substituted derivatives of (a)-(f), $L_1$, $L_2$, $L_3$ and $L_4$ represent $$-O-, -S- \text{ or } -\underset{R}{N}-$$

wherein R is hydrogen atom or an alkyl group having a carbon number of not more than 10, respectively, p and q are 2 or 3, respectively, r is an integer of 1-3, m and n are an integer of 1-7, respectively.

The giant heterocyclic compound of the above formula selectively incorporates the particular cation into voids of its cyclic structure and forms a complex therewith according to the following reaction formula:

wherein L is the giant heterocyclic compound, $M^{n+}$ is a monovalent or polyvalent cation, and K is a stability constant (complex-forming equilibrium constant) indicating the degree of complex formation and the stability of the resulting complex.

According to the invention, the giant heterocyclic compound selectively forming a complex with a particular cation is used for each of particular cations to be measured. In this case, the selectivity of the giant heterocyclic compound for the formation of complex can be expressed as a ratio of stability constant of the complex with the cation to be measured at a concentration of 0.1 mole/l in water at 25° C. to stability constant of the complex with the other cation under the same conditions. That is, according to the invention, there is used the giant heterocyclic compound having the ratio of the former to the latter of not less than 2, preferably not less than 10.

The preferred giant heterocyclic compound includes, for example, dibenzo-18-crown-6, cyclohexyl-18-crown-6, dicyclohexyl-18-crown-6, dimethyldibenzo-30 crown-6against K+; cyclohexyl-21-crown-7against Cs+; cyclohexyl-15-crown-5against NH4+; dibenzo-18-crown-6, dicyclohexyl-18-crown-6 against Ag+; dibenzo-18-crown-6, dicyclohexyl-18-crown-6 against Tl$^{30}$ ; dicyclohexyl-18-crown-6 against Sr$^{2+}$; cyclohexyl-18-crown-6, dicyclohexyl-18-crown-6 against Hg$^{2+}$; dibenzo-18-crown-6, dicyclohexyl-18-crown-6 against Pb$^{2+}$; and the like.

According to the invention, the polymer having a structural unit of the giant heterocyclic compound as described above is supported as a thin film on the surface of the electrically conductive metal. As the polymer having such a structural unit of the giant heterocyclic compound, mention may be made of (a) vinyl-type polymers obtained by radical or ion polymerization of vinyl derivatives of the giant heterocyclic compound, or vinyl-type copolymers obtained by radical or ion polymerization of the above vinyl derivatives with a vinyl monomer such as styrene, methyl methacrylate, acrylonitrile or the like; (b) polyamide-type polymers obtained by polycondensation of diamino derivatives of the giant heterocyclic compound with a dibasic acid halide such as adipic acid chloride, isophthalic acid chloride, terephthalic acid chloride or the like; (c) polyester-type polymers obtained by polycondensation of dicarboxylic acid derivatives of the giant heterocyclic compound with a glycol such as ethylene glycol, tetramethylene glycol or the like; (d) polyurea-type polymers obtained by addition polymerization of diamino derivatives of the giant heterocyclic compound with a diisocyanate such as tolylene diisocyanate, hexamethylene diisocyanate or the like; (e) polyurethane-type polymers obtained by addition polymerization of diisocyanate derivatives of the giant heterocyclic compound wth a polyhydric alcohol, polybasic acid or polyvalent amine such as polypropylene glycol, adipic acid, hexamethylenediamine or the like; (f) epoxy-type polymers obtained by addition condensation of amino derivatives of the giant heterocyclic compound with a compound having in its molecule two or more epoxy groups; (g) polymers obtained by addition polymerization of the giant heterocyclic compound having an aromatic hydrocarbon residue with formaldehyde, chloral, glutaric acid or the like; and (h) polymers supporting the giant heterocyclic compound at the surface thereof by the reaction of amino derivatives of the giant heterocyclic compound with a chloromethylated polystyrene or a divinylbenzene-crosslinked chloromethylated polystyrene.

In order to make a solid sensitive film from the aforementioned polymers, there are used the following processes:

(i) The thin film of the polymer is adhered to the surface of the semiconductor through an electrically insulating adhesive such as an epoxy resin adhesive or the like;

(ii) The fine powder of the polymer is kneaded with a thermoplastic resin such as polyvinyl chloride or polystyrene containing a plasticizer and shaped into a thin film, which is adhered to the surface of the semiconductor through an electrically insulating adhesive;

(iii) The fine powder of the polymer is applied on the surface of the semiconductor in the form of a thin film with an epoxy resin adhesive and then cured; and (iv) The epoxy-type polymer belonging to the group (f) is applied in the form of a thin film at an uncured state and then cured.

Among them, the process (iv) is most preferable because the epoxy-type polymer itself has a very strong adhesive force and can easily fix the giant heterocyclic compound to the surface of the semiconductor with a high rate of the structural unit without using a binder or an adhesive.

Thus, a stable solid sensitive film is obtained different from the conventionally well-known liquid ion exchange system. The thickness of the solid sensitive film is made thin as far as possible in order to obtain a rapid response and is preferably not more than few microns.

The reference electrode member 42 and measuring electrode member 43 are inserted in the needle 41 of the syringe from the top 411 thereof so that pointed ends of the elongated cylindrical part 425 and the solid sensitive film 432 provided on the measuring electrode member 43 are located near the opening 412 of the needle 41. In order to prevent the rocking, damage and the like of both electrode members 42, 43, they are fixed to the needle 41 through an adhesive 44. Moreover, it is preferable to locate the elongated cylindrical part 425 and solid sensitive film 432 at a position slightly inward from the opening of the needle so as to prevent the damage of them due to the contacting with other instruments during the transportation or use. Numeral 431 is a lead wire of the measuring electrode member 43.

The ion selective electrode assembly A of the above construction can simply and rapidly measure the concentration or activity of, for example, $K^+$ by dipping the opening of the needle 41 into a sample solution.

The invention will be described below with reference to an experimental example.

Into a needle of a syringe with 18G (outer diameter 1.2$\phi$, length 38 mm) was inserted a microelectrode encapsulated with reference electrode member and measuring electrode member having a specification shown in the following Table 1. With the resulting electrode assembly, a drain current was measured in a sample solution having various adjusted concentrations of potassium chloride.

The sample solution was constantly held at pH=8.7 with tris(hydroxymethyl) aminomethane and hydrochloric acid while adjusting its ionic strength.

TABLE 1

| | Term of each part | Specification |
|---|---|---|
| Reference electrode member | Internal reference electrode of Ag—AgCl | To the end of Ag wire with a diameter of 0.3 $\phi$ is adhered AgCl over a length of 8 mm. |
| | Supporting tube (glass) | 1.55 $\phi$, length 18–26 mm |
| | Elongated cylindrical part (glass) | 0.1–0.12 $\phi$, length 40 mm |
| | Standard solution | lithium trichloroacetate (5M) |
| Measuring electrode member | Field-effect ion sensor | To a gate region of field-effect transistor made from N-type Si wafer of 200 $\mu$m thickness is fixed a diamino-type polymer of dibenzo-18-crown-6 together with Epicoat 828 (trade name, epoxy resin). Film thickness 0.7 $\mu$m |
| | Insulative coating | Epoxy resin |

Figure 5:
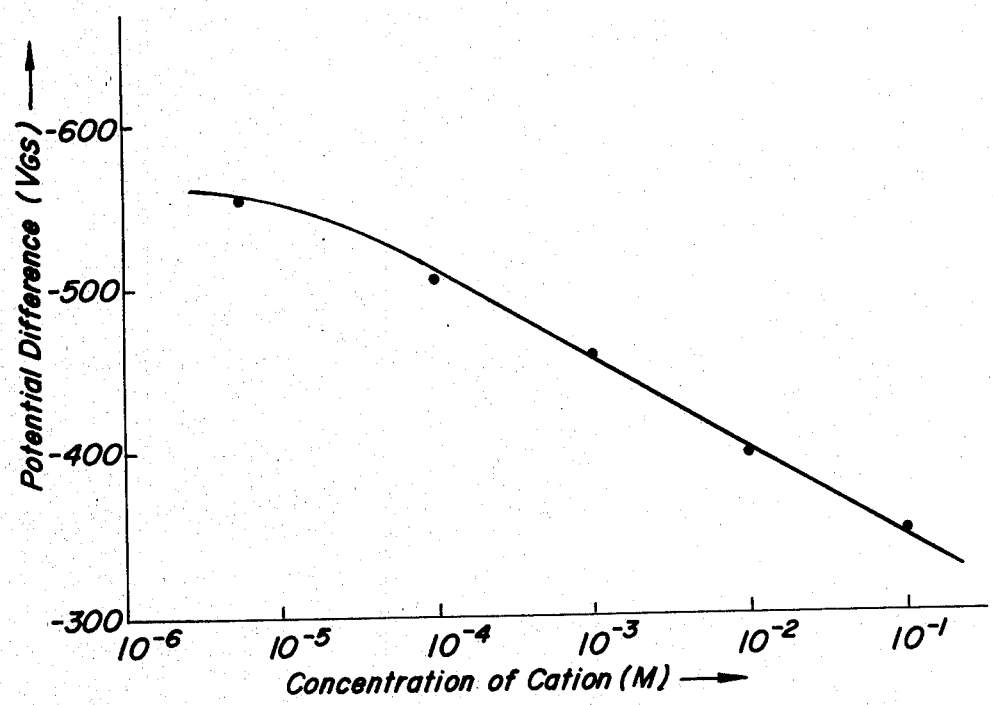
FIG. 5 is a graph showing an example of results measured by the sensor according to the invention, wherein an abscissa represents a mole concentration of K+ ion and an ordinate represents a potential difference between gate electrode and source electrode calculated from a drain current.

The result thus measured is shown in FIG. 5. As seen from FIG. 5, there is established a straight line relationship between the $K^+$ concentration and a potential difference calculated from the measured drain current within a range of $K^+$ concentration of $10^{-1}$–$10^{-4}$ mole according to the Nernst equation:

$$E = \frac{RT}{2F} \ln a_{K^+}$$

wherein $a_{K^+}$ is an activity of $K^+$ in the sample solution. That is, the electrode element according to the invention is effective for selectively measuring the concentration or activity of $K^+$.

As previously mentioned, the electrode assembly according to the invention is so constructed that the reference electrode member provided with the elongated cylindrical part and the measuring electrode member are inserted into the needle of the syringe so as to locate pointed ends of the elongated cylindrical part and the measuring electrode member near the opening of the needle and at the same time the solid sensitive film having a $K^+$ selectivity is formed on the end of the measuring electrode member to form a small-sized microelectrode element. Consequently, the $K^+$ concentration can be simply and rapidly measured even if the sample solution is used in a small amount enough to dip the opened end portion of the needle therein. Further, the measuring electrode member is possessed of the solid sensitive film different from the conventional system of liquid membrane type ion electrode, so that the durability becomes longer.

According to the invention, the surface potential of the insulative coating can be measured different from the prior art for the measurement of potential difference, so that there is taken no notice of the conductivity of ion selective film and there can be used a measuring device with a low input impedance.

Since the pointed end of the measuring electrode member is passed through the needle and is located near the opened end thereof, it makes possible to selectively measure only the $K^+$ concentration in a blood or a body fluid in the same manner as used in a common syringe.

Therefore, the electrode element according to the invention can be widely applied for not only common chemical analysis but also biochemical analysis in medical treatment by changing a combination of the standard solution with the ion selective film provided on the measuring electrode member and the like. Moreover, the electrode element according to the invention is light, small in size and portable, so that the measurement can be easily performed at any time and place and also an amount of a solution to be tested becomes very small.

What is claimed is:

1. In an ion selective field-effect sensor selectively sensitive to a particular cation to be measured, the improvement characterized by using a polymer having a structural unit of a giant heterocyclic compound, which selectively forms a complex with said particular cation, as an ion selective film provided on a surface of a field-effect semiconductor, wherein said polymer is between said giant heterocyclic compound and a member selected from the group consisting of vinyl polymers obtained by radical or ion polymerization of vinyl derivatives of the giant heterocyclic compound; vinyl copolymers obtained by radical or ion polymerization of such a vinyl derivative with a vinyl monomer; a polyamide polymer obtained by polycondensation of a diamino derivative of the giant heterocyclic compound with a dibasic acid halide; a polyester polymer obtained by polycondenstion of a dicarboxylic acid derivative of the giant heterocyclic compound with a glycol; a polyurea polymer obtained by addition polymerization of a diamino derivative of the giant heterocyclic compound with a diisocyanate; a polyurethane polymer obtained by addition polymerization of a diisocyanate derivative of the giant heterocyclic compound with a polyhydric alcohol, a polybasic acid or a polyvalent amine; an epoxy polymer obtained by the addition condensation of an amino derivative of the giant heterocyclic compound with a compound having in its molecule two or more epoxy groups; a polymer obtained by the addition polymerization of the giant heterocyclic compound which comprises an aromatic hydrocarbon group with formaldehyde, chloral or glutaric acid; and a polymer obtained by supporting the giant heterocyclic compound in polymer form by reacting an amino derivative of the giant heterocyclic compound with chloromethylated polystyrene or divinylbenzene crosslinked chloromethylated polystyrene.

2. An ion selective field-effect sensor as claimed in claim 1, wherein said giant heterocyclic compound has the following formula:

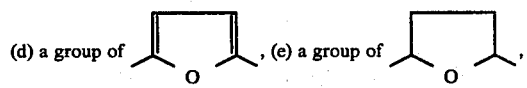

wherein X and Y are the same or different and represent
(a) a divalent aliphatic hydrocarbon residue,
(b) a divalent aromatic hydrocarbon residue,
(c) a divalent alicyclic hydrocarbon residue, (d) a group of 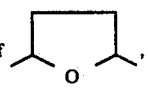, (e) a group of 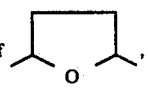, (f) a group of 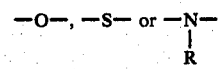 or (g) a divalent group of substituted derivatives of (a)-(f), $L_1$, $L_2$, $L_3$ and $L_4$ represent $$-O-,\ -S-\ or\ -N-\atop R$$

wherein R is hydrogen atom or an alkyl group having a carbon number of not more than 10, respectively, p and q are 2 or 3, respectively, r is an integer of 1-3, m and n are an integer of 1-7, respectively.

3. An ion selective field-effect sensor as claimed in claim 1, wherein said particular cation is $K^+$ and said giant heterocyclic compound is dibenzo-18-crown-6, cyclohexyl-18-crown-6, dicyclohexyl-18-crown-6 or dimethyldibenzo-30-crown-10.

4. An ion selective field-effect sensor as claimed in claim 1, wherein said particular cation is $Cs^+$ and said giant heterocyclic compound is cyclohexyl-21-crown-7.

5. An ion selective field-effect sensor as claimed in claim 1, wherein said particular cation is $NH_4^+$ and said giant heterocyclic compound is cyclohexyl-15-crown-6.

6. An ion selective fluid-effect sensor as claimed in claim 1, wherein said particular cation is $Ag^+$ and said giant heterocyclic compound is dibenzo-18-crown-6 or dicyclohexyl-18-crown-6.

7. An ion selective field-effect sensor as claimed in claim 1, wherein said particular cation is $Tl^+$ and said giant heterocyclic compound is dibenzo-18-crown-6 or dicyclohexyl-18-crown-6.

8. An ion selective field-effect sensor as claimed in claim 1, wherein said particular cation is $Sr^{2+}$ and said giant heterocyclic compound is dicyclohexyl-18-crown-6.

9. An ion selective field-effect sensor as claimed in claim 1, wherein said particular cation is $Hg^{2+}$ and said giant heterocyclic compound is cyclohexyl-18-crown-6 or dicyclohexyl-18-crown-6.

10. An ion selective field-effect sensor as claimed in claim 1, wherein said particular cation is $Pb^{2+}$ and said giant heterocyclic compound is dibenzo-18-crown-6 or dicyclohexyl-18-crown-6.

11. An ion selective field-effect sensor as claimed in claim 1, wherein said member selected from said group which forms said polymer between said giant heterocyclic compound is vinyl polymers obtained by radical or ion polymerization of vinyl derivatives of the giant heterocyclic compound.

12. An ion selective field-effect sensor as claimed in claim 1, wherein said member selected from said group which forms said polymer between said giant heterocyclic compound is a polyamide polymer obtained by polycondensation of a diamino derivative of the giant heterocyclic compound with a dibasic acid halide.

13. An ion selective field-effect sensor as claimed in claim 1, wherein said member selected from said group which forms said polymer between said giant heterocyclic compound is a polyester polymer obtained by polycondensation of a dicarboxylic acid derivative of the giant heterocyclic compound with a glycol.

14. An ion selective field-effect sensor as claimed in claim 1, wherein said member selected from said group which forms said polymer between said giant heterocyclic compound is a polyurethane polymer obtained by addition polymerization of a diisocyanate derivative of the giant heterocyclic compound with a polyhydric alcohol, a polybasic acid or a polyvalent amine.

15. An ion selective field-effect sensor as claimed in claim 1, wherein said member selected from said group which forms said polymer between said giant heterocyclic compound is a polymer obtained by the addition polymerization of the giant heterocyclic compound which comprises an aromatic hydrocarbon group with formaldehyde, chloral or glutaric acid.

16. An ion selective field-effect sensor as claimed in claim 1, wherein said member selected from said group which forms said polymer between said giant heterocyclic compound is a polymer obtained by supporting the giant heterocyclic compound in polymer form by reacting an amino derivative of the giant heterocyclic compound with chloromethylated polystyrene or divinylbenzene crosslinked chloromethylated polystyrene.

* * * * *

UNITED STATES PATENT AND TRADEMARK OFFICE
CERTIFICATE OF CORRECTION

PATENT NO. : 4,352,726
DATED : October 5, 1982
INVENTOR(S) : Takuo Sugano et al

It is certified that error appears in the above-identified patent and that said Letters Patent is hereby corrected as shown below:

On the title page item [73]:

Please correct the "Assignee" title to properly read:

--Takashi Mukaibo, President, University of Tokyo, Tokyo, Japan--.

Signed and Sealed this

Second Day of April 1985

[SEAL]

Attest:

DONALD J. QUIGG

Attesting Officer     Acting Commissioner of Patents and Trademarks